(12) United States Patent
Earle

(10) Patent No.: US 8,878,515 B1
(45) Date of Patent: Nov. 4, 2014

(54) CONSTANT CURRENT METAL DETECTOR

(75) Inventor: John L. Earle, Sweet Home, OR (US)

(73) Assignee: White's Electronics, Inc., Sweet Home, OR (US)

(*) Notice: Subject to any disclaimer, the term of this patent is extended or adjusted under 35 U.S.C. 154(b) by 324 days.

(21) Appl. No.: 13/235,916

(22) Filed: Sep. 19, 2011

Related U.S. Application Data

(60) Provisional application No. 61/403,598, filed on Sep. 17, 2010.

(51) Int. Cl.
- G01N 27/72 (2006.01)
- G01N 27/80 (2006.01)

(52) U.S. Cl.
CPC ................................. G01N 27/80 (2013.01)
USPC .............. 324/67; 324/326; 324/225; 324/239

(58) Field of Classification Search
CPC ....... G01N 27/72; G01N 27/80; G01N 27/90; G01N 33/20
USPC ............................ 324/67, 225, 239, 326–329
See application file for complete search history.

(56) References Cited

U.S. PATENT DOCUMENTS

| 3,528,402 | A  | * | 9/1970 | Abramowitz | 600/424 |
| 6,586,938 | B1 | * | 7/2003 | Paltoglou | 324/329 |
| 7,075,304 | B2 | * | 7/2006 | Nelson | 324/329 |
| 2008/0245628 | A1 | * | 10/2008 | Battlogg et al. | 188/267.2 |
| 2010/0148781 | A1 | * | 6/2010 | Candy | 324/329 |
| 2012/0146647 | A1 | * | 6/2012 | Candy | 324/329 |

* cited by examiner

*Primary Examiner* — Arleen M Vazquez
*Assistant Examiner* — Robert P Alejnikov, Jr.
(74) *Attorney, Agent, or Firm* — James Creighton Wray

(57) ABSTRACT

A constant current is provided to an energizing coil in a magnetic detector by charging a capacitor through a resistor from a high voltage source. Discharging of the capacitor into the energizing coil quickly increases current in the energizing coil. After the capacitor is switched off, a low voltage source maintains current constant in the energizing coil. The coil discharges its energy as a negative voltage to the capacitor. A high negative voltage source tops off the capacitor. After a delay, the capacitor discharges a negative current into the energizing coil. A negative low voltage source maintains the negative current. The negative voltage source is disconnected, and the coil discharges positive voltage into the capacitor. The high voltage source tops off the capacitor with positive voltage to repeat the cycle.

17 Claims, 4 Drawing Sheets

CONSTANT CURRENT METAL DETECTOR

BACKGROUND OF THE INVENTION

This application claims the benefit of U.S. Provisional Application No. 61/403,598, filed Sep. 17, 2010, which is hereby incorporated by reference in its entirety.

SUMMARY OF THE INVENTION

The new invention provides better target object characterization and identification while eliminating ground mineralization detection.

A constant current in the energizing coil establishes a constant magnetic field that goes from zero to a strong, but constant, field very rapidly, as in less than 10 microseconds. Target objects such as coins and other eddy current objects have an energizing time constant usually exceeding 10 microseconds, wherein the eddy currents accelerate until field equilibrium is reached in the target object.

A constant current or constant magnetic field does not produce a significant signal in a receive coil after the transition from zero to constant current from ground mineralization permeability (powdered iron or ferrite equivalent). Target object eddy currents do produce a signal of varying amplitude throughout the constant current period, depending upon eddy current charging time or inductance of the object, usually not a simple exponential due to configuration of the target object. i.e., diameter, thickness, conductivity, etc.

Methods of producing a constant current pulse, rapidly going from zero to the constant current:

1. Use a high voltage, in series with a current limiting resistor to the energizing coil. A high voltage causes current to flow in the coil and rapidly reach inductive saturation, followed by a constant current divided between the series resistor and the dc resistance of the coil. This is not efficient.

2. Use a high voltage spike from a charged capacitor to get the coil up to the desired current as fast as possible to a predetermined level, followed by a low voltage source to sustain the same current after the coil inductance has been charged. Current and field is then sustained at a constant current/field until the pulse is terminated after a period longer than the anticipated target object time constant. Target objects having time constants typically from 10 to 50 microseconds. Constant current pulse applicable here would be 100 microseconds.

These and further and other objects and features of the invention are apparent in the disclosure, which includes the above and ongoing written specification, with the claims and the drawings.

DETAILED DESCRIPTION OF THE DRAWINGS

Figure 1:
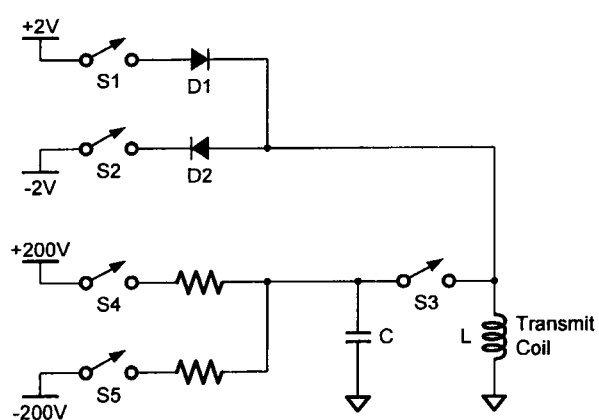
FIG. 1 is a schematic circuit diagram showing the voltage sources, resistors, diodes, capacitor and transmit coil as used in the invention.

FIG. 1 depicts the block diagram schematic. Switches shown are semiconductors, such as transistors, FET's, etc. programmed as shown in FIG. 2.

Figure 2:
FIG. 2 is a schematic representation of timing of the switches to provide the voltages and coil current of this invention.

FIG. 2 illustrates the timing sequence, with positive direction indicating the on time of each switch.

As shown in FIGS. 1 and 2, the following steps occur. The process starts with switch S4 turning on to charge capacitor C with a high voltage (+200 volts). Switch S4 is turned off.

Next, switch S3 turns on for about 4 microseconds, connecting capacitor C (0.01 Mfd) to the coil L of 0.53 Mhy. During this time, energy is transferred from the capacitor C to the coil L in a classic inductance/capacitance resonance with frequency of ½ pi, square root of LC, where L is in henries and C is in farads. For this example, f=69,000 Hz (69 Khz.) This frequency, if allowed to continue resonating, would have a period of 14.4 microseconds. But, maximum current is obtained within only ¼ of a complete cycle, giving a period of only 3.6 microseconds. When current becomes maximum, the voltage of the resonant system approaches zero, but is caught by diode D1, that sustains the current at a constant level from being turned on by switch S1 at the same time switch S3 turned on and switch S3 turns off. Thus, the desired current is achieved in less than 4 microseconds.

The desired eddy current targets typically have a charge and discharge time constant of 10 to 100 microseconds, so they are largely unaffected by this fast pulse that establishes the constant energizing field current. Once established, diode D1 sustains the coil charging current for 125 microseconds, which is long enough to energize the eddy current object. Because the current is essentially constant during this time of 3 to 125 microseconds, there is no di/dt or rate of current change that would create a signal from the ground mineralization permeability.

This is helpful in giving that same entire period of observing for eddy current target charging distortion to the constant current from 3 to 125 microseconds, producing a target signal with no permeability signal present, similar to the standard pulse decay time target response, but of opposite polarity. And additionally, because of the wide difference between magnetic remanence charging time and discharge time, there is a difference between this active but constant signal and the zero current, after the pulse traditional pulse signal, producing better characterization of the target and the magnetic remanent portion of the ground mineralization.

At the end of the 125 microsecond constant current, diode D1 current is cut off by switch S1 opening, and switch S3 closes at the same time. The coil current collapses without current through diode D1, and a large back emf charges capacitor C in the negative direction, almost reaching a negative 200 volts, and switch S3 opens leaving capacitor C nearly charged, but of opposite polarity to when it started with +200 volts through switch S4.

For the next cycle, switch S5 closes to fully charge capacitor C in the negative direction to −200 volts. Switch S5 turns off followed by switch S3 closing again and switch S2 closing the coil/capacitor resonance occur again, with the opposite polarity to induce the negative current period. Switch S3 opens as the desired negative current is achieved. Switch S2 remains closed with diode D2 maintaining the negative constant current through the 125 microsecond period.

At the end of the second 125 microsecond period, switch S2 opens and switch S3 closes and a large back emf charges capacitor C in the positive direction, almost reaching a positive 200 volts, and switch S3 opens leaving C nearly charged, to when it started with +200 volts through switch S4. Switch S4 closes briefly to fully charge capacitor C and the cycle repeats.

Thus, there is a bipolar field established, which is helpful in negating the earth's magnetic field and other noise sources. Most of the back emf is used to recharge capacitor C, making it an efficient system with little energy lost in dissipation as in a traditional pulse detector that dissipates energy through the zener breakdown of the switching device.

FIG. 2 is a schematic representation of timing of the switches to provide the voltages and coil current of this invention. The on times of closing of switches S1-S5 and the coil voltage and coil current in transmit coil L are shown.

Initially capacitor C is charged. When switch S3 is closed 10 and switch S1 is closed 12, voltage in coil L rapidly increases 14 and coil current rises 16.

When switch S3 is opened 18, constant coil current 20 is maintained from the +2v source, through switch S1 and its diode D1, shown in FIG. 1.

When switch S1 is opened 22 and switch S3 is closed 24, voltage 26 in the coil is negative, and back emf flows through switch S3 into the capacitor C. The coil current rapidly drops 28 to zero for a period of rest 29. Switch S5 is closed 30 to top off the capacitor C with a full negative voltage charge from the −200 v source. Then switch S5 is opened 31. At the end of the period of rest 29, switch S2 is closed 32 and switch S3 is briefly closed 34 and opened 36. Negative voltage energy from capacitor C is conducted to the coil L, which creates a negative voltage 38 and causes negative current to increase 40 in coil L. The negative current is maintained constant 42 from the −2v source through switch S2 and diode D2.

Switch S2 is opened 44 and switch S3 is closed 46 and coil voltage 47 is discharged from the coil L through switch S3 to the capacitor C, charging the capacitor with positive voltage 47 from coil L. Switch S3 is opened 48, holding the charge on the capacitor. Switch S4 is closed 50 connecting the capacitor to the +200v positive voltage source to fully charge the capacitor, whereupon S4 is opened 52.

The cycle repeats as shown with important constant positive current 20 in the coil L for 125 microseconds, followed by a zero current rest time 29 of about 375 microseconds, followed by a constant negative current 40 in the coil, followed by a rest time 49 of zero current in the coil.

Figure 3:
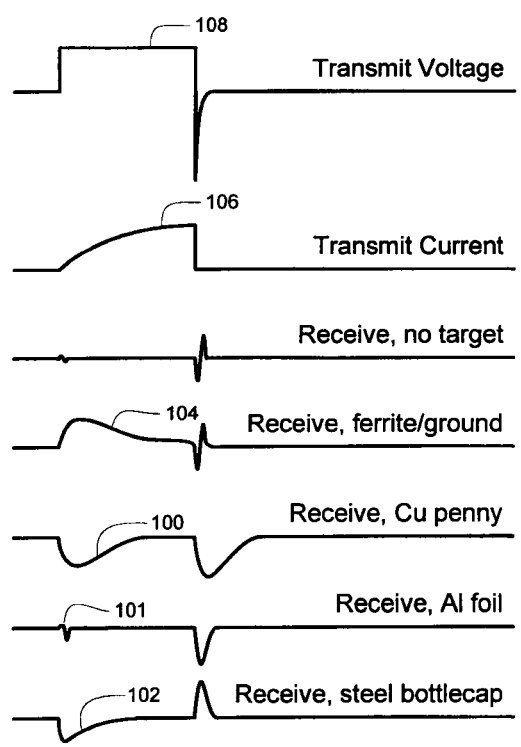
FIG. 3 shows timing of transmit voltage and current and received signals from the ground and objects using a traditional pulse detector.
Figure 4:
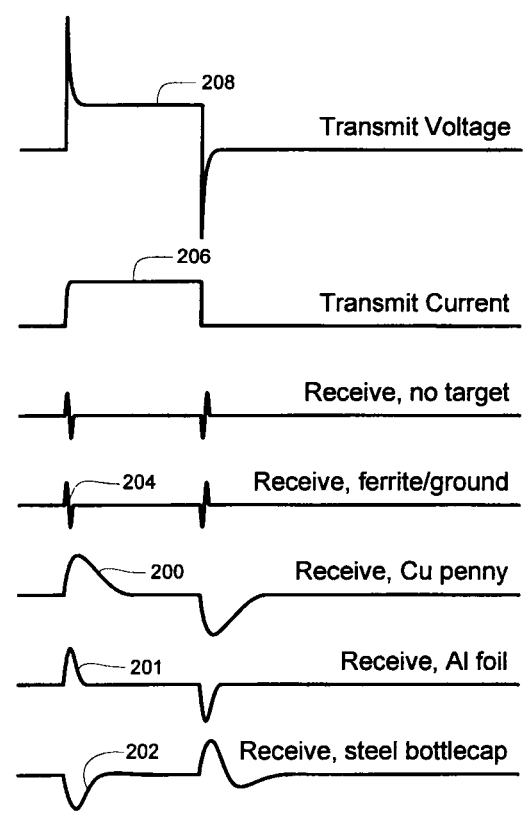
FIG. 4 shows timing of transmit voltage and current and received signals from the ground and objects using the constant current pulse technology.

FIG. 3 depicts the traditional pulse detector, showing how received signals 100, 101, 102 from targets are obscured by ferrite/ground signals 104 during the active current 106 and voltage 108 time. FIG. 4 shows how received target signals 200, 201 and 202 are revealed and not obscured by ferrite/ground signals 204 in this invention in both the active constant current time 206 and active voltage time 208.

New features and advantages of the invention include the following.

A constant current establishes a constant magnetic field in a metal detector energizing coil that allows eddy current target objects to charge up according to their own time constant. Change of field during that time is detected, and amplitude during that time characterizes an eddy current object while permeability mineralization is ignored.

The system utilizes a high voltage and energizing coil to rapidly establish constant current and field.

A high voltage is discharged for a short period of time into an energizing coil, followed by a low voltage to sustain the established constant current for period exceeding the charging time of the eddy current target object to be detected.

The system utilizes a capacitor charged to a high voltage and discharged into an energizing coil, followed by a low voltage to sustain the established constant current for a period longer than the eddy current charging time.

At the end of the constant current period a switch is closed to charge the capacitor with the opposite polarity pulse from the collapse at the end of the constant current.

The invention uses the alternating polarity to energize the energizing coil.

The invention uses subtraction of alternate polarity target responses to cancel out earth's constant single polarity field and other spurious responses.

The invention provides interrogating eddy current target objects and the remanent ground signals during constant but non zero current and during the zero current following the active current time with comparison to further delineate and identify ground and target objects.

The invention differs substantially from a traditional voltage pulse detector that rely on a zero constant current, after the energizing pulse to look for the target object discharging field, not the charging field effects. The charging current in a traditional pulse detector is an asymptotic ramp, which creates a large ground mineral response, which is why target data is not looked for during pulse charging time.

In a traditional multiple frequency (sine wave or equivalent) detector data samples are taken at only one point or phase of each frequency, since there is only one point in every 180 degrees of sine wave where di/dt is zero. Thus, an additional frequency is needed for each detection sampling point that will yield target information without detection of ground mineralization which occurs whenever di/dt is briefly zero.

With constant current, di/dt is a constant, and no ground mineralization permeability signal is detected throughout the energizing time. That means that eddy current target responses can be looked for Throughout the entire constant current period with an infinite number of samples to thoroughly characterize the target object better than with a finite number of frequencies, as in traditional multiple Frequency detector.

While a traditional pulse detector characterizes the target discharge characteristics, it is a fading signal after the energizing current has returned to zero, which is weaker than the charging characteristics observed during the constant current charging of this application.

Some ground mineralization exhibits not only the fleeting permeability of the ground mineralization, as does ferrite and some fine iron powders, but it may also exhibit some "viscous magnetic remanence" (VMR), which is like a short time permanent magnetization of the ground mineralization. VMR typically fades rapidly at first, after the energizing field ends and then fades more slowly in a very long time period. This is different than an eddy current target object discharge, which produces a more nearly exponential discharge characteristic. By taking multiple samples throughout the constant current time period, prior to encountering an eddy current target, the VMR can be identified and separated from the desired eddy current target discharge characteristics.

In a multiple frequency sine wave (or equivalent) detector, the VMR slews the apparent (ferrite) phase angle, so that ground nulling, which is now a composite, has to be adjusted at each frequency to eliminate ground response in order to distinguish the desired eddy current target object. With the constant current system described herein, there is no ferrite response and only the VMR (if it exists) has to be identified and subtracted, or otherwise dealt with to get the eddy current target object characteristics.

While the invention has been described with reference to specific embodiments, modifications and variations of the invention may be constructed without departing from the scope of the invention, which is defined in the following claims.

I claim:

1. A metal detector method comprising establishing constant current and a constant magnetic field in a metal detector energizing coil that allows eddy current target objects to charge up according to their own time constant by charging a capacitor to a high voltage, and discharging the high voltage from the capacitor into the energizing coil, followed by applying of low voltage to the energizing coil, detecting change of field during that time in a receive coil and detecting amplitude during that time, and characterizing the eddy current target objects while ignoring permeability mineralization.

2. The metal detector method of claim 1, further comprising utilizing a high voltage, series resistor to rapidly establish a constant current field in the energizing coil.

3. The method of claim 1, further comprising applying the high voltage discharged for a short period of time into the energizing coil, followed by applying the low voltage to the energizing coil and sustaining the established constant current for period exceeding the charging time of the desired eddy current target object to be detected.

4. The method of claim 1, further comprising closing a switch at the end of the constant current period to charge the capacitor with the opposite polarity pulse from the collapse at the end of the constant current.

5. The method of claim 4, further comprising utilizing the alternating polarities to energize the energizing coil.

6. The method of claim 5, further comprising subtracting the alternate polarities from received coil target responses to cancel out earth's constant, single polarity field and other spurious responses.

7. The method of claim 1, further comprising interrogating received signals of eddy current target objects and remanent ground signals during constant but non zero current excitation and during zero current excitation following the active current time and comparing the received signals, thereby further delineating and identifying ground and target objects.

8. The method of claim 7, further comprising characterizing the receive coil ground response signals prior to encountering eddy current target and subtracting the ground response from subsequent receive coil response signals with eddy current target signals present, and providing eddy current target response from the subtracting.

9. The method of claim 7, further comprising additional interrogating of receive coil signals during initial high voltage current charging and discharging points for further ground permeability, remanence and eddy current target characterization.

10. Apparatus comprising a metal detector having an energizing coil, a capacitor charged by a high voltage source and discharged into the energizing coil and for rapidly energizing the coil, a low voltage source connected to the coil for establishing and maintaining constant current in the energizing of the coil magnetic field in an adjacent substance that allows eddy current target objects to charge up according to their own time constant and sustaining the established constant current and having a receive coil detecting change of the magnetic field current target objects to charge up according to their own time constant and sustaining the established constant current and having a receive coil detecting change of the magnetic field during that time and amplitude during that time that characterizes the eddy current object while permeability mineralization is ignored.

11. The apparatus of claim 10, wherein the high voltage source is connected to the capacitor through a series resistor and the capacitor is connected to the energizing coil to rapidly establish a constant current field.

12. The apparatus of claim 10, further comprising a switch closed at the end of the constant current period to charge the capacitor with an opposite polarity pulse from the collapse of energy in the energizing coil at the end of the constant current period of time.

13. The apparatus of claim 12, further comprising alternating polarity energy sources connected to the energizing coil.

14. The apparatus of claim 13, further comprising subtractors of alternate polarity in the receive coil from target responses to cancel out earth's constant, single polarity field and other spurious responses.

15. The apparatus of claim 10, further comprising sampling for interrogating receive coil eddy current target objects and the remanent ground signals during constant but non zero current excitation and during zero current excitation following the active current time and a comparator comparing the received signals, thereby further delineating and identifying ground and target objects.

16. The apparatus of claim 15, further comprising sampling for characterizing receive coil ground response prior to encountering eddy current target and subtracting said response from subsequent receive coil response with eddy current target present, providing eddy current target response.

17. The apparatus of claim 15, further comprising sampling for additional interrogation of receive coil during initial high voltage current charging and discharging points for further ground permeability, remanence and eddy current target characterization.

\* \* \* \* \*